（12) United States Patent
Rontal

(10) Patent No.: US 7,749,221 B2
(45) Date of Patent: Jul. 6, 2010

(54) RETRACTABLE ELECTROSURGICAL ELECTRODE

(76) Inventor: Daniel A. Rontal, 926 Bird, Birmingham, MI (US) 48009

( * ) Notice: Subject to any disclaimer, the term of this patent is extended or adjusted under 35 U.S.C. 154(b) by 703 days.

(21) Appl. No.: 11/466,522

(22) Filed: Aug. 23, 2006

(65) Prior Publication Data

US 2007/0049922 A1 Mar. 1, 2007

Related U.S. Application Data

(60) Provisional application No. 60/710,522, filed on Aug. 23, 2005, provisional application No. 60/763,693, filed on Jan. 31, 2006.

(51) Int. Cl.
*A61B 18/18* (2006.01)
(52) U.S. Cl. ............... 606/41; 606/45; 606/49
(58) Field of Classification Search ............. 606/41–45, 606/49
See application file for complete search history.

(56) References Cited

U.S. PATENT DOCUMENTS

| | | | | |
|---|---|---|---|---|
| 3,699,967 A * | 10/1972 | Anderson | ............ | 606/37 |
| 4,699,140 A * | 10/1987 | Holmes et al. | ............ | 606/107 |
| 4,931,047 A * | 6/1990 | Broadwin et al. | ............ | 604/22 |
| 5,330,492 A * | 7/1994 | Haugen | ............ | 606/167 |
| 5,334,198 A * | 8/1994 | Hart et al. | ............ | 606/52 |
| 5,360,427 A * | 11/1994 | Majlessi | ............ | 606/41 |
| 5,380,321 A * | 1/1995 | Yoon | ............ | 606/41 |
| 5,527,313 A * | 6/1996 | Scott et al. | ............ | 606/51 |
| 5,645,076 A * | 7/1997 | Yoon | ............ | 604/165.01 |
| 6,569,161 B2 * | 5/2003 | Zappala | ............ | 606/41 |
| 2002/0147447 A1 * | 10/2002 | Long | ............ | 606/41 |
| 2003/0163123 A1 * | 8/2003 | Goble et al. | ............ | 606/34 |
| 2003/0216733 A1 * | 11/2003 | McClurken et al. | ............ | 606/51 |

* cited by examiner

*Primary Examiner*—Linda C Dvorak
*Assistant Examiner*—Benjamin Lee
(74) *Attorney, Agent, or Firm*—Gifford, Krass, Sprinkle, Anderson & Citkowski, P.C.

(57) ABSTRACT

A manually supported electrosurgical device comprises an elongated electrode supported for motion within an insulated housing so that in one position its operating end extends from the housing into a surgically useful position and in another position its operating end is retracted within the housing. A spring has one end connected to the housing and the other end connected to the spring so as to normally urge it to the retracted position. A manually actuable trigger supported on the housing may be depressed to force the electrode against the spring force so that its operating end extends out of the housing. When the pressure on the trigger is removed, the spring forces the electrode back into the housing. When depressed, the trigger connects the electrode to a radio frequency generator.

8 Claims, 3 Drawing Sheets

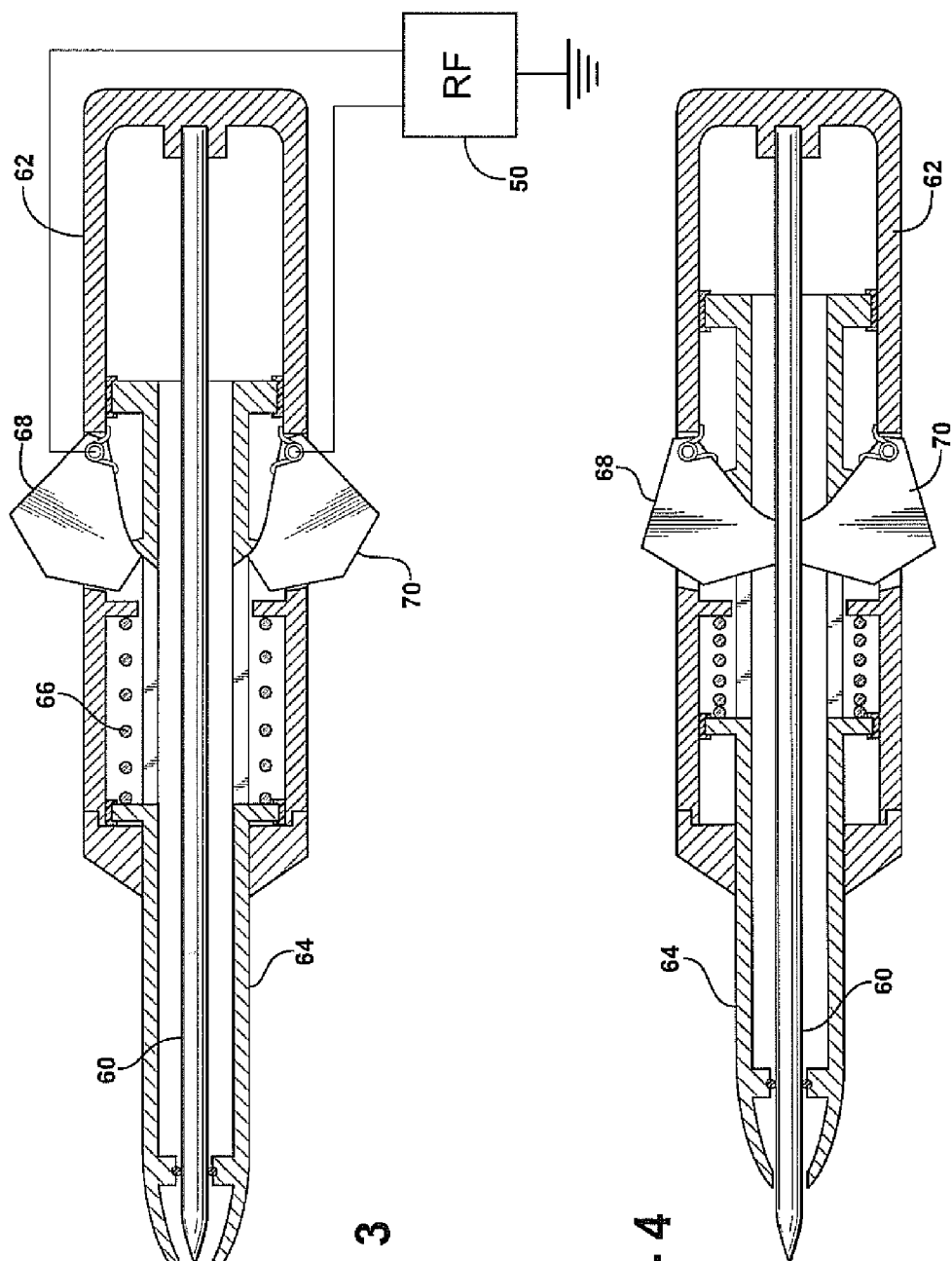

RETRACTABLE ELECTROSURGICAL ELECTRODE

RELATED APPLICATIONS

This application claims priority of U.S. Provisional Patent Application Ser. No. 60/710,522 filed Aug. 23, 2005, and U.S. Provisional Patent Application Ser. No. 60/763,693 filed Jan. 31, 2006, both of which are incorporated herein by reference.

FIELD OF THE INVENTION

This invention relates to an electrode or probe for use with electrosurgery apparatus such as electrocutting or electrocoagulating systems and more particularly to an electrode which is normally covered by a housing and may be extended from the housing to allow a surgeon to perform an electrosurgical process and automatically retracts at the end of the process.

BACKGROUND OF THE INVENTION

In electrosurgery a radiofrequency generator is adapted to be connected to a handheld or robotically held probe or electrode which the surgeon brings into contact with tissue. Depending upon the frequency of the generated current, the electrode may either cauterize the tissue or, at a higher frequency, cut the tissue.

When the electrode tip is accidentally brought into contact with body tissue on the patient or the surgeon, the tissue may be punctured or otherwise damaged in a potentially serious manner.

It has been proposed to provide an electrosurgical electrode with an insulating housing that allows the tip to be retracted within the housing to prevent accidental damage by contact with the tip. For example, in U.S. Pat. No. 6,569,161, springs within the device apparently urge the tip into an extended position with respect to the housing. After use the electrode is retracted back into the housing by pressing the tip of the electrode against a surface to cause a needle to retract back into the housing. It is apparently locked into this retracted position until released by a switch 24. Accordingly, the normal position, or default position, of the device is with the electrode extended and it may be retracted into the housing by forcing the extending spring into a retracted position. This design appears to be inherently unsafe in that the failure of the trigger mechanism will allow the electrode to be extended into its potentially dangerous position.

SUMMARY OF THE INVENTION

The present invention is therefore directed toward an electrosurgical electrode or probe which is normally surrounded by an insulated housing so as to avoid accidental injury to the patient and surgeon. When the surgeon desires to utilize the probe, he depresses a trigger which either extends the electrode from the housing, to an operative position, or allows a section of the housing to retract, exposing the electrode tip, and simultaneously connects the electrode to a conductor connected to the generator so as to provide cutting or coagulating currents to the electrode.

When the trigger is released the electrode is automatically drawn back into its retracted position or the cover section extends over the tip. Thus, in the absence of a depressing force on one of the triggers of the device, the probe will be safely disposed in its retracted position.

While retractable electrodes formed in accordance with the present invention could be designed to either cut or coagulate, a preferred embodiment of the invention is operative to alternatively cut or coagulate. The unit is equipped with a pair of triggers which may be depressed by the surgeon. By depressing one of the triggers, the electrode is extended and simultaneously connected to a conductor providing coagulating currents. Upon release of the trigger, the electrode automatically retracts within the housing. By depressing the other trigger, the electrode is extended from the housing and connected to a conductor which provides cutting currents from the radiofrequency generator. Again, when the cutting trigger is released the electrode automatically retracts within the housing.

In the preferred embodiment of the invention the proximal end of the electrode is connected to one end of an extension spring having its other end connected to the housing. Depression of either one of the triggers exerts a force on a cam connected to the needle, forcing the electrode out of the housing and extending the spring so that it imposes a retracting bias on the electrode. When the trigger is released the spring automatically returns the electrode to within the housing. In the preferred embodiment the electrode is retained in a pencil type housing so that the surgeon may hold it in one hand and conveniently depress either the cutting or the coagulating triggers with one motion.

In an alternative embodiment of my invention, the electrode is fixed in a proximal end of the housing and a telescoping distal end is biased by a spring to surround the electrode tip. When a trigger is depressed the distal end is retracted against the spring bias, exposing the electrode end for use.

BRIEF DESCRIPTION OF THE DRAWINGS

Other objects, advantages and applications of the present invention will be made apparent by the following description of the preferred embodiment of the invention. The description makes reference to the accompanying drawings in which:

FIG. 3 is a sectional view of a second embodiment of my invention with a retractable section of the housing in extended position covering the tip of the electrode; and FIG. 4 is a sectional view of the embodiment of FIG. 3, with the housing end retracted, exposing the electrode tip for use.

DETAILED DESCRIPTION OF THE INVENTION

Figure 1:
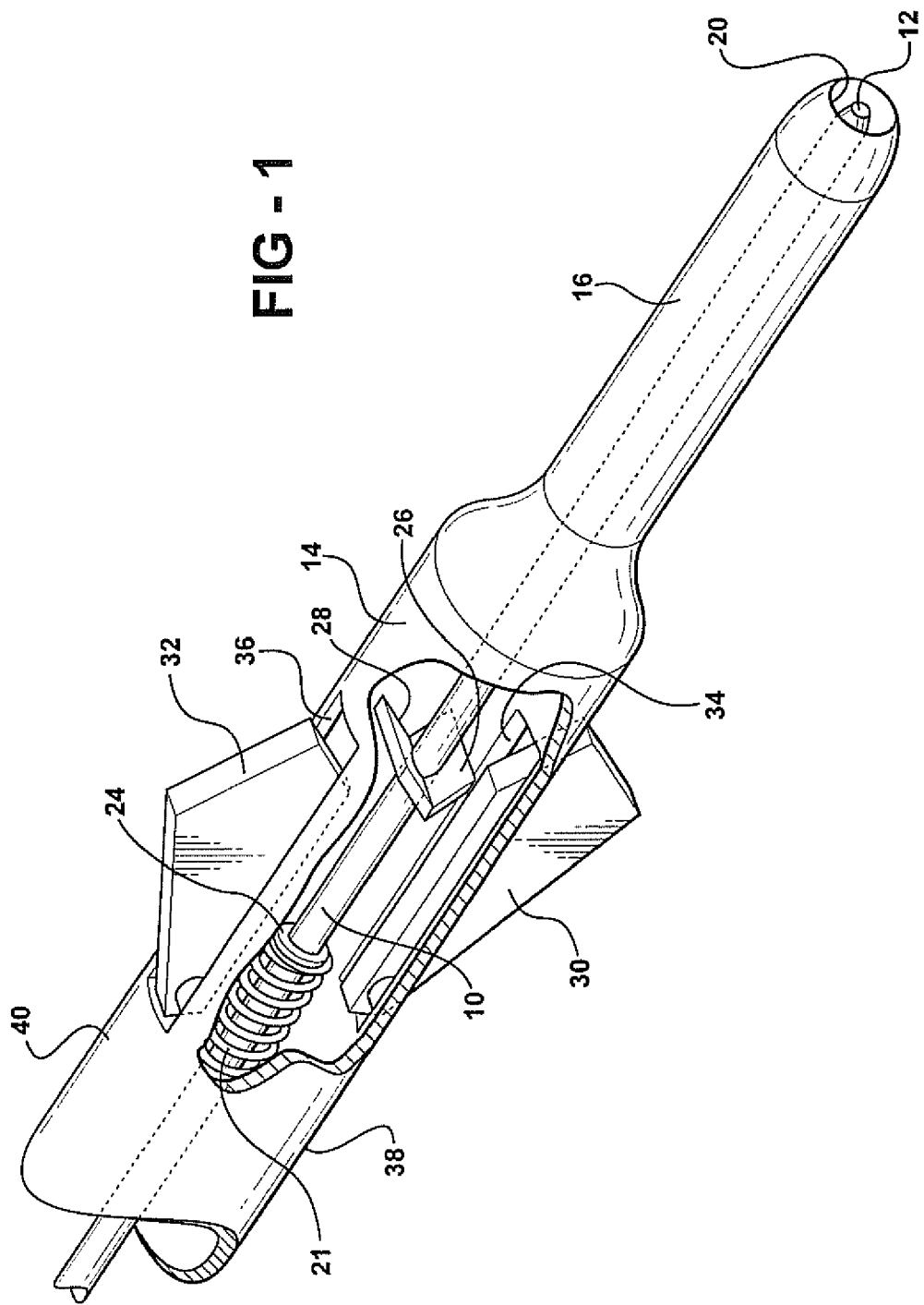
FIG. 1 is a perspective view of the cauterizing electrode holder and the electrode, partially broken away for purposes of illustration.
Figure 2:
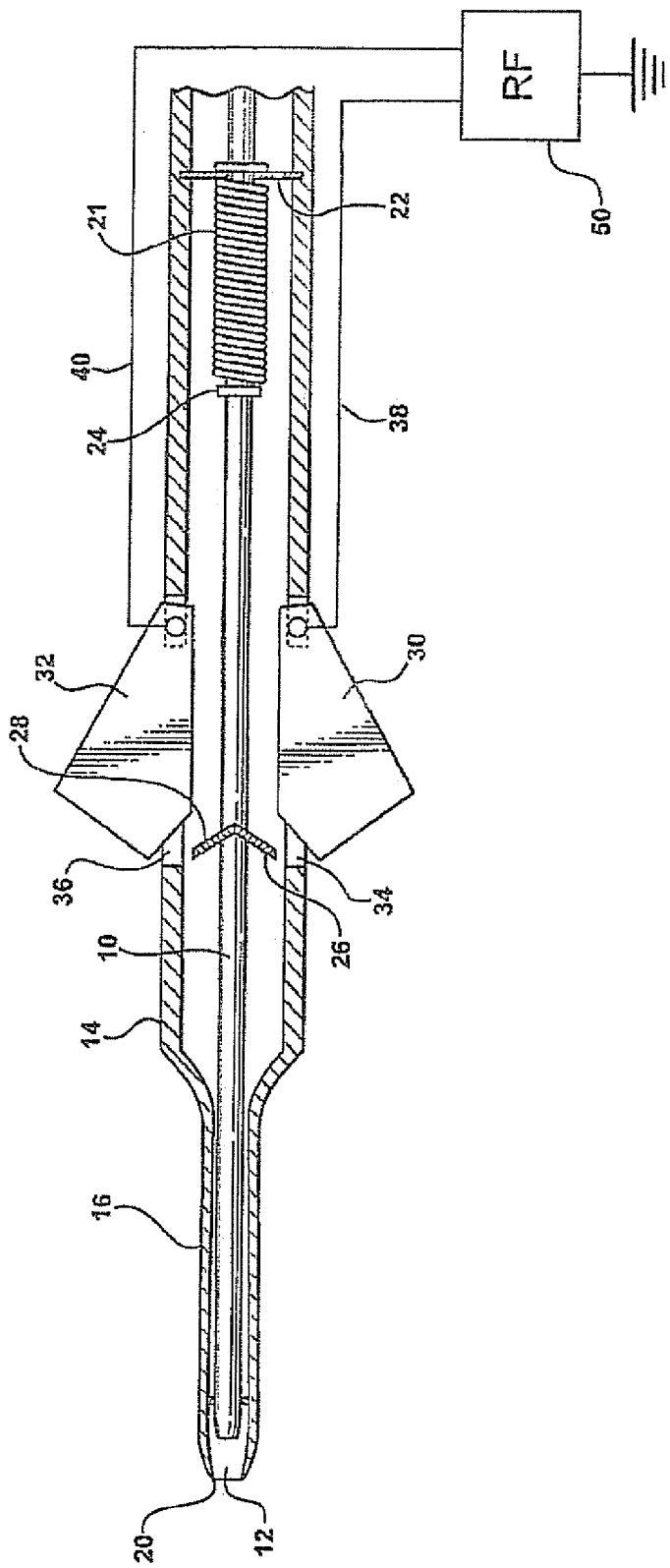
FIG. 2 is a cross-sectional view of the retractable electrode device taken along line 2-2 of FIG. 1.

Referring to the drawings, the preferred embodiment of the present invention employs an elongated cylindrical electrode 10 having a tip 12 and a cylindrical body. It is normally disposed within an insulating elongated cylindrical housing 14 having a smaller diameter distal section 16 surrounding the electrode and having an opening 20 at its distal end from which the tip 12 may project. A spiral extension spring 21 has its proximal end fixed to a disc 22 formed at an end of the housing 14 and its forward end connected to the electrode 10 through a pin 24. The electrode further has a pair of inclined trigger surfaces or cams 26 and 28 connected midway along its length.

A pair of triggers 30 and 32 are each pivotably supported at the proximal ends of openings 34 and 36 which are formed in diametrically opposed sides of the needle body 14, midway along its length. A forward surface of each of the triggers 30 and 32 lies over a respective one of the cam surfaces 26 and 28. When one of the triggers is depressed downwardly toward the needle, its trigger surface forces against the surface 26 or 28 to force the electrode tip 12 forward, out of the opening 20. This extends the spring 21.

The electrodes 30 and 32 are respectively connected to conductors 38 and 40 which extend along the housing body. The conductor 38 connects to the RF generator 50 to provide a cutting current while the conductor 40 connects to the RF generator to provide a coagulating current. Alternatively, a single RF generator capable of emitting either electrocautery or electrocutting currents could be provided along with appropriate switches to provide one current or the other when the appropriate trigger is depressed. The generator is preferably grounded and the patient is grounded so that current is applied to the area contacted by the electrode 12. Other conventional arrangements may be employed to complete the electrosurgical circuit. When the trigger is released, the spring 21 retracts the electrode to within the housing and disconnects it from the associated RF generator.

The device of the present invention thus automatically disconnects electrical currents from the electrode 10 when manual pressure is removed from the associated trigger and the spring 21 moves the electrode into its retracted position within the insulated housing 14. Additionally, the same manual pressure which extends the electrode into operating position connects the electrode to the appropriate generator for either cutting currents or coagulating currents.

In a second embodiment of my invention, illustrated in FIGS. 3 and 4, an electrode 60 has its proximal end fixed to the proximal end 62 of a housing, which acts as a handle device. A cylindrical shield 64 is slidably supported relative to the handle section and is normally extended to cover and shield the electrode 60 by a spring 66, as shown in FIG. 3.

When either the cauterizing trigger 68 or the cutting trigger 70 is manually depressed as shown in FIG. 4, it connects the electrode to the appropriate terminal of the power supply 50 and forces the shield section 64 to retract, exposing the tip of the electrode 60 and compressing the spring 66. When the trigger is released, the electrode is disconnected from the power supply and the shield 64 is extended by the spring to cover the tip.

Other variations of the invention, employing other mechanisms, could be constructed within the scope of the appended claims.

Having thus described my invention, I claim:

1. A retractable electrosurgical device comprising:
    an elongated electrode having a tip at its distal end and having a cam fixed along its length;
    an elongated housing for the electrode having an opening at one end;
    a spring having one end connected to the housing and the other end connected to the electrode to urge the electrode tip to a first position wherein the tip is disposed within the housing;
    a radio frequency current generator having a first output of electrocautery currents and a second output of electrocutting currents;
    a first manually depressible trigger pivotably supported relative to the housing, operative, when depressed by a manual force, to connect the electrode to said first output of electrocautery currents and to impose a force on the cam to move the electrode against the spring force to a second position wherein the tip is extended from the housing, and when the manual force is removed, to allow the electrode to retract within the housing under the force of the spring and disconnect the electrode from the first output of electrocautery currents; and
    a second manually depressible trigger pivotably supported relative to the housing, operative, when depressed by a manual force, to connect the electrode to said second output of electrocutting currents and to impose a force on the cam to move the electrode against the spring force to a second position wherein the tip is extended from the housing, and when the manual force is removed, to allow the electrode to retract within the housing under the force of the spring and disconnect the electrode from the second output of electrocutting currents.

2. The retractable electrosurgical device of claim 1 wherein a single radio frequency generator is capable of providing either electrocautery or electrocutting currents.

3. The retractable electrosurgical device of claim 1, wherein separate radio frequency generators are provided to generate either the electrocautery currents or the electrocutting currents.

4. The electrosurgical device of claim 1 in which the spring is a tension spring.

5. The electrosurgical device of claim 1 wherein the first and second triggers are supported on opposite sides of the housing.

6. An electrosurgical device comprising:
    an elongated electrode having a tip at its distal end;
    an elongated insulating housing for the electrode having an opening at its distal end, the housing having a pair of telescoping proximal and distal sections with the proximal end of the electrode fixed to the proximal section, with the telescoping sections normally extended relative to one another so that the distal section of the housing covers the electrode tip;
    a radio frequency generator having a first output of electrocautery currents and a second output of electrocutting currents; and
    a first manually actuable trigger pivotably supported on the housing, having a first, manually depressed position in which the distal section of the housing is retracted so that the electrode tip extends out of the housing opening into operating position and the electrode is connected to the first output of electrocautery currents, and a second, nondepressed position, in which the electrode tip is covered by the housing and the electrode does not receive current from the generator; and
    a second manually actuable trigger having a manually depressed position in which the distal section of the housing is retracted so that the electrode tip extends out of the housing opening into operating position and the electrode is connected to second output of electrocutting currents and a second, nondepressed position, in which the electrode tip is covered by the housing and the electrode does not receive current from the generator.

7. The electrosurgical device of claim 6 further comprising a spring disposed between the two housing sections biasing the sections toward extended position and manual actuation of the trigger forces the two sections to move to retracted position against the spring bias.

8. The electrosurgical device of claim 6 wherein the first and second triggers are supported on opposite sides of the housing.

* * * * *